United States Patent [19]

Zimmermann et al.

[11] 4,292,408

[45] Sep. 29, 1981

[54] MASS AND A METHOD OF PREPARING SAME OF LIVING CELLS OF ORGANISMS FOR ADSORBING METAL IONS FROM A PHYSIOLOGICAL SOLUTION, AND EMPLOYMENT OF THE MASS FOR ENRICHING METALS

[75] Inventors: Ulrich Zimmermann; Günter Pilwat, both of Jülich, Fed. Rep. of Germany

[73] Assignee: Kernforschungsanlage Jülich Gesellschaft mit beschränkter Haftung, Jülich, Fed. Rep. of Germany

[21] Appl. No.: 19,436

[22] Filed: Mar. 12, 1979

Related U.S. Application Data

[63] Continuation-in-part of Ser. No. 753,474, Dec. 22, 1976, abandoned.

[30] Foreign Application Priority Data

Dec. 24, 1975 [DE] Fed. Rep. of Germany ....... 2558750

[51] Int. Cl.$^3$ ...................... C12N 13/00; C12N 1/20; C12N 1/12; C02F 3/00
[52] U.S. Cl. ................................... 435/173; 435/253; 435/257; 435/262
[58] Field of Search ............... 204/195 B, 180 R, 299; 210/2; 435/173, 253, 254, 255, 257, 262

[56] References Cited

U.S. PATENT DOCUMENTS

| | | | |
|---|---|---|---|
| 3,095,359 | 6/1963 | Heller | 435/30 |
| 4,081,340 | 3/1978 | Zimmermann et al. | 204/180 R |

FOREIGN PATENT DOCUMENTS

| | | |
|---|---|---|
| 2405119 | 9/1975 | Fed. Rep. of Germany . |
| 737282 | 5/1932 | France . |

OTHER PUBLICATIONS

Pilwat, et al., "Dielectric Breakdown Measurements of Human and Bovine Erythrecyte Membranes Using Benzyl Alcohol as a Probe Molecule", *Biochim. Biophys. Acta*, vol. 406, (1975), pp. 424–432.

Belton, et al., "Effects of Pharmacalagical agents on the Electrical Responses of Cells of *Nitella Flexilis*", *Chem. Abstracts*, vol. 76, No. 3, p. 68, (1972), Abs. No. 10704n.

*Primary Examiner*—Thomas G. Wiseman
*Attorney, Agent, or Firm*—Becker & Becker

[57] ABSTRACT

A mass, and method of preparing such mass, and using the same for adsorbing metal ions from a physiological solution by means of living cells suspended in the solution. The cells suspended in the solution at a density of up to 20% by weight are exposed to an electric field of such intensity and over such a period of time that the membrane of the cells will be so changed that substances present in the interior of the cells and having a diameter within the range of from 2 to 50 A, such as potassium and proteins, pass from the interior of the cells into the physiological solution. The electric force or intensity is limited in such a way that the changes in the membrane of the cells can be healed by regeneration of the cells. The mass is introduced into the aqueous solution, such as sea water, lake water or waste water, and left therein until the mass as adsorbed therefrom the metal at a desired concentration, whereupon the mass is separated from the aqueous solution.

3 Claims, No Drawings

MASS AND A METHOD OF PREPARING SAME OF LIVING CELLS OF ORGANISMS FOR ADSORBING METAL IONS FROM A PHYSIOLOGICAL SOLUTION, AND EMPLOYMENT OF THE MASS FOR ENRICHING METALS

This is a continuation-in-part of co-pending parent application Ser. No. 753,474-Zimmerman et al filed Dec. 22, 1976, now abandoned.

The present invention relates to a method of preparing a mass of living cells of organisms, which cells have cell walls and are suspended in a physiological solution, for adsorbing metal ions from a physiological liquid. The present invention also relates to the mass produced in conformity with this method. The invention furthermore concerns a particularly advantageous utilization of the mass according to the invention.

Cells of organisms have the capability to adsorb metal ions which are contained in a physiological liquid. If cells of organisms are introduced into a physiological liquid which contains metal ions, only those adsorbing areas of the cell become effective which are located at the surfaces of the cells.

It is, therefore, an object of the present invention so to treat the adsorbing areas within the cells that they can be used for the adsorption of metal ions contained in a physiological liquid in order in this way to be able to utilize the adsorption capability of the cells of organisms for technical purposes.

Expressed differently, it is an object of the present invention to provide a method of producing a mass of living cells of organisms which have cell walls and are suspended in a physiological liquid, the mass being able to be used in the manner of an adsorbing substance for adsorbing metal ions from a physiological liquid, which method can be carried out in a simple and economical manner and will result in a product having a high adsorbing capability.

These and other objects and advantages of the invention will appear more clearly from the following examples set forth further below.

The method according to the present invention is characterized primarily in that the cells suspended in the physiological solution at a density of up to about 20 percent by weight are exposed to an electric field of such a force and such a duration of the effect of this force that the membranes of the cells will be changed in such a way that those substances present in the interior of the cells which have a diameter within the range of from 2 to 50 angstrom, as for instance potassium or proteins, will pass from the interior of the cells into the physiological solution while the electric force and the duration of its effect are so limited that the changes in the membranes of the cells can be healed by regeneration of the cells. By the indicated weight of the cells, the weight of fresh cells is meant.

The invention is based on the finding that the adsorption capability of cells of organisms for metal ions is drastically increased when the adsorbing areas in the interior of the cells are made accessible for the metal ions in the physiological liquid without destruction of the cells. The invention is furthermore based on the finding that due to the influence of the electric field, the membrane of the cell is opened while the cell wall remains unchanged so that the cell wall retains its function of supporting the membrane. The capability of the cells to live will thus not be affected.

Through the thus created openings, substances will pass from the interior of the cells into the physiological solution and also substances from the physiological solution will pass into the interior of the cells so that when the cells are introduced into a liquid containing metal ions, also the metal ions will pass into the interior of the cells, which means that the adsorbing areas in the interior of the cells will become effective. The adsorbing capability of the cells for metal ions is thus considerably increased. In this connection it is also possible by the influence of an electromagntic radiation—as for instance X-rays, a mechanical radiation—such as ultrasound radiation, or a corpuscular radiation—as for instance neutron radiation, to produce openings in the cell membranes. Furthermore it is possible by means of osmotic forces to bring about the intended changes in the membranes of the cells while in this connection it may become necessary prior thereto to remove the cell walls.

The invention is furthermore based on the finding that an increase in the permeability of the membranes of the cells and thus an opening of the cells is brought about by an electric puncture of the cells. In this connection, the cells are introduced into a physiological liquid forming an electrolyte solution, and two electrodes extending into the liquid receive electric voltage which is just sufficient to effect the electric puncture of the cells. The electric voltage at which this is realized is designated as electric puncture voltage. The membrane of a living cell which in its normal condition is not electrically conductive will then become electrically conductive. The magnitude of the electric puncture voltage at which the increase in the permeability occurs depends primarily on the electric properties of the membrane of the cell, on the elastic properties of the membrane, on the thickness of the membrane of the cell and on the size of the cell.

It is expedient to utilize a field strength of the electric field of from about 1 to 20 kV/cm. The procedure may be such that the physiological solution containing the cells is passed through the effective range of the electric field. It is furthermore expedient to expose the cells to a pulsed electric field with a pulse duration of from 1 $\mu$sec up to a duration which is just below the duration at which the cells would be destroyed by heat. The field strength of the electric field is so selected that the electric puncture voltage will build up on the membrane of the cells. The number of pulses amounts to about from 2 to 10 $\mu$sec.

In order to realize that the mass produced in conformity with the present invention will in spite of a regeneration of the cells retain its full adsorption capability during its utilization, the mass is either directly following its production introduced into the physiological liquid which contains the metals to be adsorbed, or the mass is produced directly in the liquid which contains the metals. However, it may also be expedient to store the mass after its preparation in undercooled condition at about 0° C. up to its utilization. In this way it will be possible to maintain for several days the high adsorption capability of the mass according to the invention.

A particularly advantageous modification of the method according to the present invention consists in that protein synthesis inhibitors, such as cycloheximide or the like, in a concentration of about $10^{-6}$ Mol/l are introduced into the physiological solution. This brings about that the changes effected in the cells by the method according to the invention and thus also the openings in the membrane of the cells will be retained to a great extent because of the absence of the regeneration process and that the mass according to the invention will thus also at normal temperature retain its high adsorption capability over a longer period of time.

The mass prepared in conformity with the present invention has an adsorption capability which is at least by the factor 2 higher than the adsorption capability of cells of the same type which are in the original condition and are suspended in a physiological solution. For the adsorption of copper from a physiological solution the adsorption capability of the mass according to the invention is, when used in a suspension density of 0.1 percent by weight of cells in the solution and with a concentration of copper in the solution of 1 $\mu$Mol/l at least twice as high as is the case when utilizing a comparable quantity of cells of the same type in their original condition and when using the same suspension density and the same concentration of copper in the solution.

According to a particularly advantageous method, the mass according to the invention is utilized for enriching metals from an aqueous solution, such as sea water, fresh water, waste water, and the like, which aqueous solution contains at least 0.5 mM/l of magnesium and or calcium and potassium ions. The cells are introduced into the aqueous solution simultaneously having characteristics of a physiological solution compatible for living cells and the cells are left therein until the metals in the desired concentration have been adsorbed by the mass, whereupon the mass is separated from the aqueous solution.

It is thus possible in an advantageous manner to utilize the mass according to the invention for the recovery of metals which are urgently needed in industry, such as uranium and lithium. These metals are present in sea water in large quantities, but in a low concentration or dilution, so that heretofore it has not been possible to recover these metals from sea water in an economical way. The employment of the mass according to the present invention will in view of its high adsorption capability for the metals, uranium and lithium permit an economical recovery of these metals. In this connection the economy of the method can still further be improved by starting the production of the mass according to the invention with cells or organisms, for instance chlorella or dunaliella algae, or sea water bacteria MB 22, which are grown in nitrate and phosphate waste waters as they are obtained, for instance in connection with the production of detergents. This makes it additionally possible in a very economical way to recover metals from industrial waste waters.

The invention will now be explained in greater detail in the following examples:

EXAMPLE 1

Chlorella algae with a density of about 10 percent by weight were introduced into a liquid which contains 0.5 percent by weight of NaCl and thus is a good conducting electrolyte solution. By a device for producing an electric high voltage, four times in a row at intervals of a few as an electric voltage pulse of an electric voltage of about 10 kV/cm and a pulse duration of 10 $\mu$seconds was applied to two flat square-shaped platinum electrodes which extended into the solution and were of the dimensions 3 cm $\times$ 3 cm. the distance between the electrodes amounted to 1 cm.

For effecting an adsorption of uranium from sea water, the cells were centrifuged out of the solution, and about 5 grams of cells were introduced into 100 liters of sea water and were left therein while being agitated for about 24 hours; the sea water contained 430 mM/l NaCl, 50 mM/l $MgCl_2$, 9.5 mM/l KCl, 10 mM/l CaCl, 2 $\mu$M/l lithium and 0.03 $\mu$M/l uranium. The enrichment factor ascertained at the end of this 24 hour period for uranium in the cells, with respect to the concentration of uranium in the sea water, was $10^6$.

EXAMPLE 2

Sea water bacteria MB 22 were introduced into a medium of the following composition: 400 mM/l NaCl, 10 mM/l KCl, 20 mM/l $MgSO_4$, 15 mM/l $MgCl_2$, 3 mM/l $Na_2HPO_4$, 0.7 percent caseinhydrolysate and 0.01 percent yeast extract. It should be noted that the term "MB 22" is known to an expert in this field for a certain type of sea water bacteria from *J. Bacteriol,* July 1975, Volume 123, Pages 294–301. This publication discloses the isolation of sea bacteria MB 22 from sea water.

The growth of the bacteria takes place over night at 30° C. while being gased with carbogene. The gas mixture "carbogene" (Trademark designation Carbogene) consists of 95% of $O_2$ and 5% of $CO_2$. Subsequently thereto, the cells were withdrawn from the nutrient medium by centrifuging for 10 minutes at 10,000 g, were washed twice with a medium of the above described composition, but without the substrates caseinhydrolysate and yeast extract, and were then brought to a suspension density of about 20 percent by weight. By a device for generating an electric high voltage, in the suspension 10 kV/cm were discharged by means of a condenser of 4 $\mu$F which corresponds to a pulse duration of about 40 $\mu$sec.

Thereupon the suspension at a weight ratio of 1:100 was introduced into a medium of the above described composition, but again without the substrates and with a copper ion content of 1 $\mu$m/l, and was agitated at room temperature for two hours.

For ascertaining the enriching factor of copper in the cells, the cells were centrifuged out of the solution, were ashed in a tracerlab-cold incinerator (Trademark designation Tracerlab), and the copper was chemically ascertained in the residue. A comparison of the thus ascertained copper content in the cells with the copper content in the starting solution showed that an enrichment by the factor 3 had taken place.

A co-pending application Ser. No. 762,320-Zimmerman et al filed Jan. 25, 1977, now U.S. Pat. No. 4,081,340-Zimmerman et al issued Mar. 28, 1978 concerns procedural features for treatment of cells including a method for production of the mass as well as the mass that is produced but does not in any way concern enriching of metals contained in a physiological solution. The co-pending application Ser. No. 762,320, now U.S. Pat. No. 4,081,340, requires an introduction of complex formers in cells to find heavy metal ions. Accordingly, the features disclosed by the co-pending Ser. No. 762,320, now U.S. Pat. No. 4,081,340, belonging to the assignee of the present invention can be considered practically identical as to the known features for increasing the permeability of the skin of cells of living things with the measures for production of a mass of cells of living things. It is also correct that the mass product in the known manner is practically identical with the mass mentioned in the present case.

To the extent that a teaching can be taken from the co-pending Ser. No. 762,320, now U.S. Pat. No. 4,081,340, belonging to the assignee of the present invention to utilize the product mass for enriching of metal ions, difference in essential features exist distinguishable from the teaching of the present invention. Moreover, there must additionally be proceeded on the basis that first complex formers must be inserted in the cells with the increased permeability, the change of the cells must thereupon be healed in order to enclose the complex formers and not until then is the so-formed mass used for increasing of metal ions; the present invention now provides the teaching for inserting the produced mass directly for enriching of metal ions. The present invention proceeds on the basis of the recognition that in contrast to the previously known teaching, the produced mass itself can be inserted as adsorber material for enriching of metal ions, whereby the adsorber locations existing in the cell interior are used directly for adsorption of metal ions.

This teaching according to the present invention is believed novel beyond any doubt. The present invention is also a technical advance when compared with the previously known teaching since the present invention is more simple to handle than the previously known teaching and the present invention gets along without utilization of expensive complex formers. The present disclosure, however, is also inventive. From the co-pending application Ser. No. 762,320, now U.S. Pat. No. 4,081,340, belonging to the assignee of the present invention, there is not once recognizable any showing or suggestion to make obvious the teaching of the present invention. Moreover, the average man skilled in the art is strengthened in his belief by way of the teaching of the co-pending Ser. No. 762,320, now U.S. Pat. No. 4,081,340, that special measures must be undertaken, for example the inserting of complex formers if the average man skilled in the art is to apply the produced mass for enriching of heavy metal ions. The known teaching consequently is believed to be directly opposite to the teaching of the present invention.

The method for enriching of metal ions should be considered novel for protection including the features to expand the method for enrichment of metal ions in order to further the method steps for use of protein-synthesis-inhibitors.

The wording "physiological solution" states nothing more than that there is involved a solution compatible for living cells of living things in which accordingly living cells of living things can be kept without encountering damage. The concept "physiological" pertains accordingly both to the osmolarity of the solution and also to the substances existing in the solution. Since the average man skilled in the art, however, is aware of this interrelationship, the average man skilled in the art knows also how in the individual case the physiological solution must be composed so that cells of living things can be kept therein. A statement concerning the density of the solution is not necessary for this purpose and also would be hardly possible. Since for carrying out the method according to the invention cells are provided accordingly which have a cell wall and accordingly are more capable of resistance with cells without a cell wall, the selection of the physiological solution is not critical. Since the percentage by weight is set forth, the statement for the quanitity of the cells to be introduced in the solution is independent of the density of the solution itself and accordingly clearly determined.

The wording "regenerating said cells" should be clarified thereby that the cells must still be capable of regeneration after utilization of the electric field. In other words, the influence or effect of the electric field cannot be permitted to be so strong so that the changes of the cell skin effected by way of the electrical field can no longer be healed. Accordingly, no additional measures are necessary (aside therefrom that the healing steps are accelerated by way of nominal heating of the solution containing the cells).

In comparison with the co-pending Ser. No. 762,320, now U.S. Pat. No. 4,081,340, the teaching of the present invention is based upon the recognition that cells of living things treated in the known manner are suitable in a salient manner for enrichment of heavy metal ions without introduction of complex formers. Consequently, there should be considered as the sole contribution of the present invention to have provided the teaching for applying of the cells treated in the known manner without introduction of complex formers for enrichment of heavy metal ions.

The present invention emphasizes the utilization of the produced mass for enrichment of heavy metal ions from an aqueous solution because beyond any doubt this involves a novel and unobvious utilization of the produced mass.

The following comments concern the "physiological" solution as well as the definition of the watery or aqueous solution.

A page 2687 from "Römpp Chemielexiko ," Franskh'sche Verlagshandlung, Stuttgart/1974 shows that the average man skilled in the art understands a physiological sodium chloride solution to be a solution which as an isotonic solution corresponds to the physio- logical-osmotic body conditions. In this lexicon citation, a physiological sodium chloride solution is defined as a sterilized 0.9% water solution of NaCl which corresponds as isotonic solution as to physiological-osmotic body conditions and subcutan or intravenous as carrier fluid for medicine and used with electrolyte loss (for instance after stronger bleeding) E physiological salt solution. This is a solution accordingly which is also adapted to the conditions prevailing in membranes of the cells of living things. The expression "physiological solutions" is to represent or state nothing different. The average man skilled in the art should understand fully and competely the concept of "physiological" in the aforementioned scope. Agreement is expressed with the recitation of the different watery solutions as consisting of a group of physiological solutions. Under these circumstances, the attention must be directed to the fact that the mentioned solutions come into question or consideration only insofar as the concern involves physiological solutions in the aforementioned sense.

The present invention also covers the use of protein synthesis inhibitors and emphasis for protection is directed to a use of the cell mass for enrichment of heavy metal ions.

It is, of course, to be understood that the present invention is, by no means, limited to the specific examples set forth above, but also comprises any modifications within the scope of the appended claims.

What is claimed is:

1. A method specifically for removing metal ions contained in an aqueous solution, the method comprising the steps of:

providing a treating solution which is physiologically compatible with living cells;

preparing a mass of single cell microorganisms, each having a cell wall with a membrane supported thereby, the mass weighing approximately 20% of the physiologically compatible solution;

suspending the mass of cells in the solution;

exposing the treating solution with the mass of cells suspended therein to an electric field having an intensity in the range of 1 to 20 KV/CM for a period of time sufficient to increase the porosity of the cell membranes wherein the increased porosity allows molecules within the cells and having diameters in the range of 2 to 50 Ångström units to pass through the cell walls and into the treating solution;

limiting the exposure to a level which permits regeneration of the membranes after termination of the exposure;

removing the cells from the treating solution;

adsorbing the metal ions in the aqueous solution onto the cells by suspending the cells in the aqueous solution; and removing the adsorbed metals from the aqueous solution by removing suspended cells therefrom, the aqueous solution having the desired metal ions include uranium ions, wherein the microorganisms are selected from the group consisting of chlorella algae, dunalliela algae, sea water, bacteria grown in nitrate and phosphate waste waters, wherein the exposure step comprises pulsing the treating solution four times at an intensity of about 10 KV/CM with a pulse duration of about 10 $\mu$sec, wherein the removing step comprises centrifuging the solution to separate the microorganisms from the solution and wherein the adsorbing step comprises suspending the microorganisms.

2. A method according to claim 1, which includes the step of introducing a protein synthesis inhibiting substance having a concentration of about $10^{-6}$ Mol/l into said aqueous solution compatible for living cells and simultaneously having physiological solution characteristics.

3. A method according to claim 2, which includes the step of using cycloheximide as protein synthesis inhibiting substance and thus retaining high absorption capability over a longer period of time.

* * * * *